United States Patent

Rygaard

[11] Patent Number: 6,066,148
[45] Date of Patent: May 23, 2000

[54] METHOD AND ANASTOMOTIC INSTRUMENT FOR USE WHEN PERFORMING AN END-TO-SIDE ANASTOMOSIS

[75] Inventor: Jørgen A. Rygaard, Gentofte, Denmark

[73] Assignees: Oticon A/S, Hellerup, Denmark; Bernafon AG, Berne, Switzerland

[21] Appl. No.: 09/142,682
[22] PCT Filed: Apr. 30, 1996
[86] PCT No.: PCT/DK96/00197
§ 371 Date: Sep. 16, 1998
§ 102(e) Date: Sep. 16, 1998
[87] PCT Pub. No.: WO97/40754
PCT Pub. Date: Nov. 6, 1997

[51] Int. Cl.[7] .................................................. A61B 17/08
[52] U.S. Cl. ............................................................. 606/153
[58] Field of Search ........................... 606/153, 151–152, 606/154–159, 139, 219; 227/176.1, 179, 178, 180, 177

[56] References Cited

U.S. PATENT DOCUMENTS 5,119,983  6/1992  Green et al. .
5,205,459  4/1993  Brinkerhoff et al. .
5,292,052  3/1994  Bilotti et al. .
5,366,462  11/1994  Kaster et al. ........................... 606/153
5,695,504  12/1997  Gifford, III et al. ................... 606/153

Primary Examiner—Michael Buiz
Assistant Examiner—Vikki Trinh
Attorney, Agent, or Firm—Larson & Taylor

[57] ABSTRACT

A method and apparatus for establishing an end-to-side anastomosis by using an instrument (501) is disclosed. The instrument has a passage (502D) for a bypass vessel, terminated by a circumferential anvil (502A, 503B), about which the end of the bypass vessel may be everted and then inserted through an anastomosis opening in a second vessel, such as a coronary artery. After insertion, the tissue edges to be joined are first clamped together by clamping slides (505) and then stapled together by stapling plungers (506) so as to interconnect the two vessels. The stapling plungers (506) are arranged to move at an angle to the passage (502D) instead of parallel to it. With this arrangement, it is possible to use a greater number of staples than has been possible in previous related methods. Preferably also, the instrument is adapted to be divided lengthwise of the passage (502D).

7 Claims, 7 Drawing Sheets

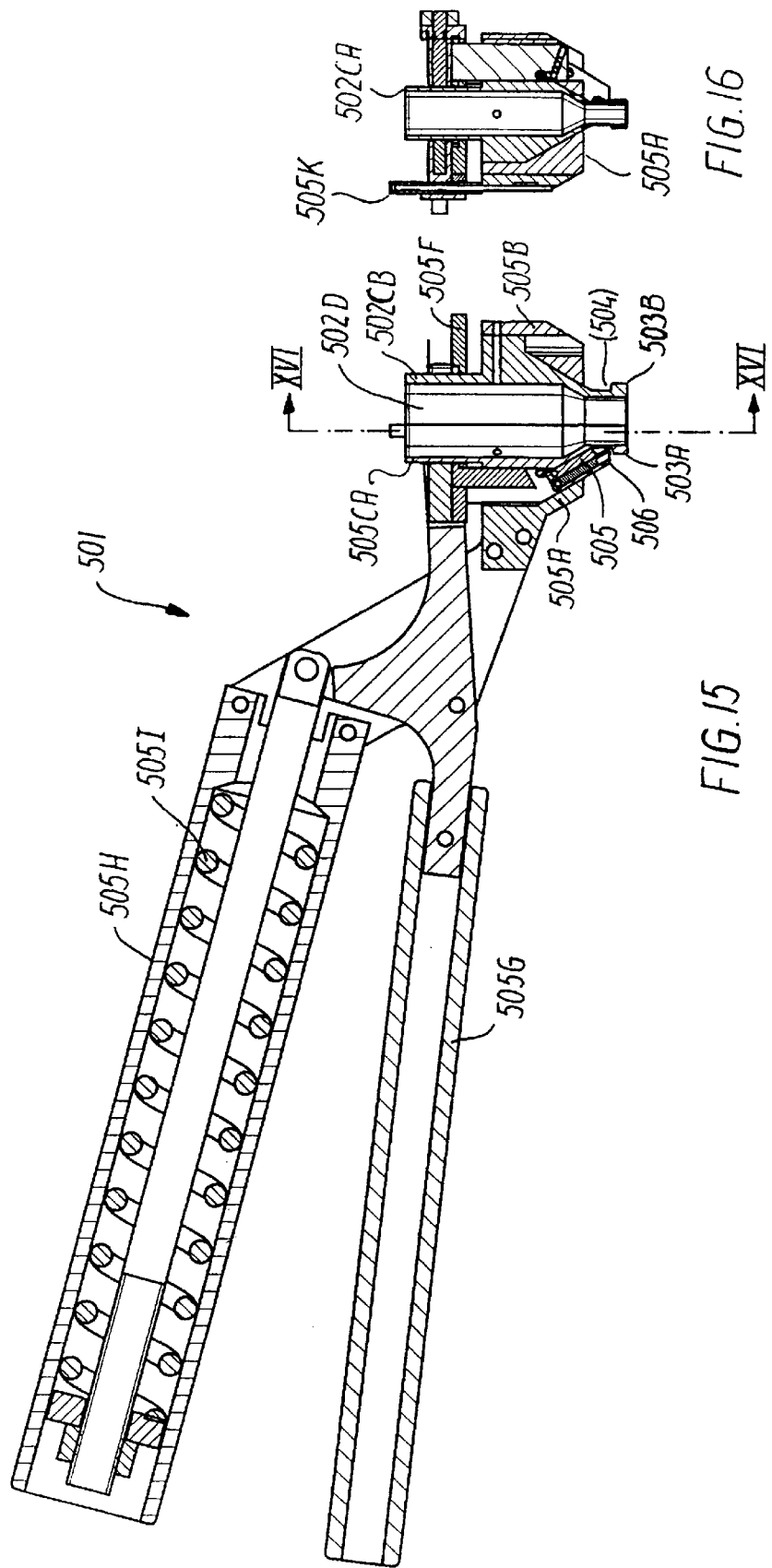

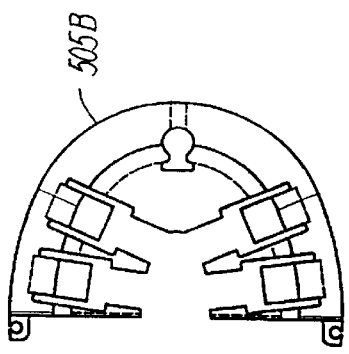
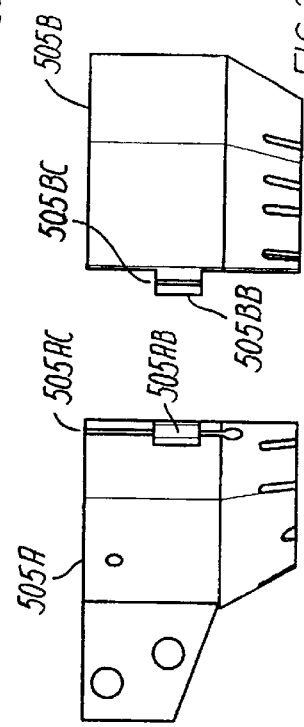
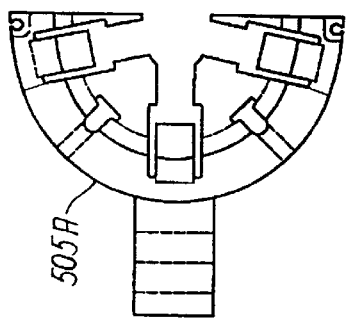
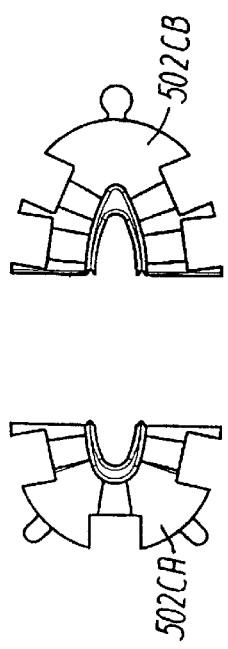
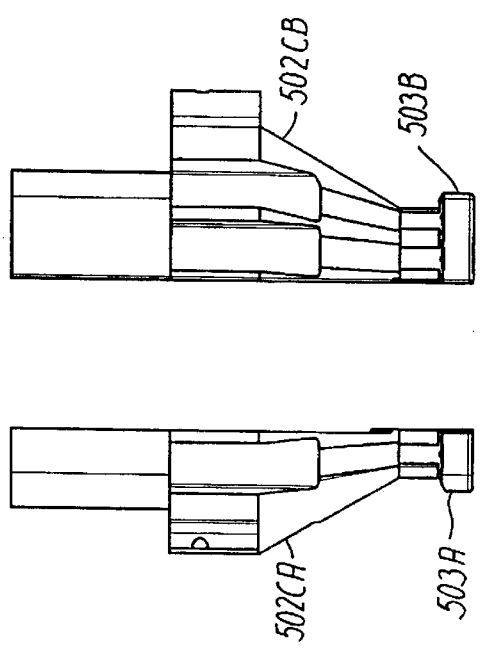
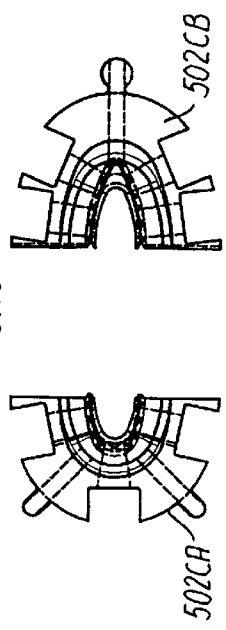

METHOD AND ANASTOMOTIC INSTRUMENT FOR USE WHEN PERFORMING AN END-TO-SIDE ANASTOMOSIS

TECHNICAL FIELD

The present invention relates to a method of connecting an end region of a first vessel to the side of a second vessel by carrying out an end-to-side anastomosis.

BACKGROUND ART

A method of this kind is described in the international application PCT/DK95/00430. In this previous method, the stapling plungers as well as the associated clamping members were adapted to move in directions substantially parallel to the passage, in which the graft vessel was placed in readiness for establishing an end-to-side anastomosis with e.g. a coronary artery. With such an arrangement, the number of staples as well as their mutual closeness were limited by the purely mechanical need for guiding the stapling plungers in their operative movement, with the result that in the "seam" connecting the two vessels, there could be substantial distances between adjacent staples.

DISCLOSURE OF THE INVENTION

It is the object of the present invention to provide a method of the kind referred to above, with which it is possible to use the instrument for establishing anastomoses with a greater number of staples and with smaller distances between adjacent staples than has been possible with the previously known method referred to above. This object is achieved by proceeding as set forth hereinbelow. In this manner, the guideways for the stapling plungers will mostly be situated at a greater "radius" than the staple-bending recesses, so that there is ample space for forming these guideways in a greater number than previously, to converge at very small mutual distances at the staple-bending recesses in the anvil.

The present invention also relates to an anastomotic instrument for carrying out the method according to the invention, and this instrument is characterized by the anastomotic instrument also described hereinbelow.

Advantageous embodiments of the method and the anastomotic instrument according to the invention, the effects of which—beyond what is self-evident—are explained in the following detailed part of the present description.

BRIEF DESCRIPTION OF THE DRAWINGS

In the following detailed part of the present description, the invention will be explained in more detail with reference to the exemplary embodiments of an anastomotic instrument according to the invention shown in the drawings, in which

FIG. 15 is a sectional side view of the complete instrument,

FIG. 16 is a sectional view taken along the line XVI—XVI in FIG. 15,

FIGS. 17–19 show a core member with associated anvil tube as viewed from the rear, side and front, respectively, and FIGS. 20–22 show a housing likewise as viewed from the rear, side and front, respectively.

Please note that the "front end" of the instrument is the end comprising the part in operation being in contact with the anastomosis being established, in this case the anvil 503A, 503B.

DESCRIPTION OF THE PREFERRED EMBODIMENTS

As mentioned above, the embodiment shown in FIGS. 1–8 of the anastomosis instrument according to the invention subject of the application PCT/DK95/00430 constitutes a simplified version with the primary purpose of explaining the invention; this does not, however, preclude the possibility of using this embodiment in actual practice.

Figure 1:
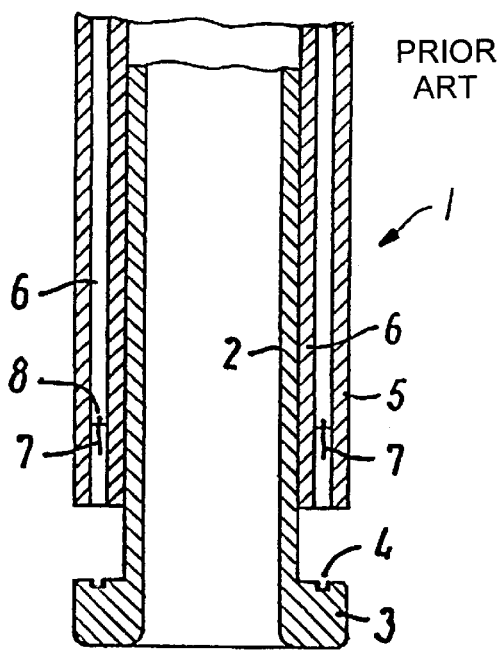
FIGS. 1–8 show the process of performing an end-to-side anastomosis using an anastomotic instrument according to the invention subject of the application PCT/DK95/00430 referred to initially, FIGS. 1–7 being drawn in a highly simplified manner for ease of understanding, FIGS. 9–11 in perspective and with certain parts cut away show a practical embodiment of an anastomotic instrument according to the present invention with the various possible relative positions of the relatively movable parts.

Thus, FIG. 1 shows an anastomosis instrument 1 consisting of three main components that are movable relative to each other in the longitudinal direction, i.e. in the direction shown as the vertical direction in FIG. 1:

an anvil tube 2, a clamping tube 5, and a set of stapling plungers 6.

On its lower end, the anvil tube 2 carries an anvil 3, the upper side of which is provided with a number of staple-bending recesses 4 adapted to cooperate with and bend an equal number of staples 7, in the situation shown in FIG. 1 being temporarily held lightly in an equal number of staple-holding recesses 8 formed in the lower ends of the stapling plungers 6.

Figure 2:
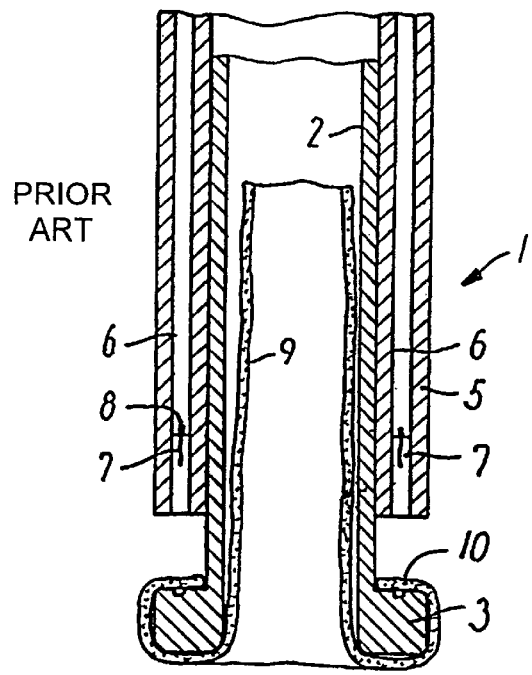

FIG. 2 shows the situation, in which the instrument is made ready for use by the operating surgeon. As mentioned initially, the anastomosis instrument shown is primarily developed for use when performing coronary bypass operations, and to this end, a bypass vessel 9—that may be a vein taken from some other part of the patient's body—has been inserted in the anvil tube with its lower end everted about the anvil 3 and with its end region 10 covering the staple-bending recesses 4 in the upper surface of the anvil 3. At this point it should be noted that the bypass vessel 9 may have a considerably larger circumference than the inside of the anvil tube 2, consequently lying more or less folded in the longitudinal direction in the latter, for which reason the action of everting its end region 10 about the anvil 3 does not necessarily entail undue stretching of the bypass vessel 9.

Figure 3:
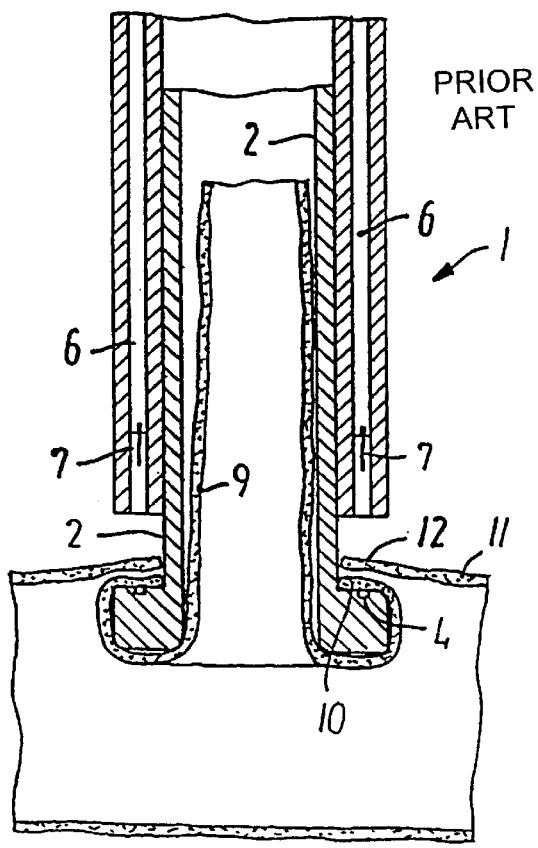

FIG. 3 shows the instrument having been made ready as shown in FIG. 2 inserted in an opening in a coronary artery 11, said opening having an edge region 12 which, due to the elasticity of the tissue of the coronary artery 11, will embrace the anvil tube 2 in a location close to the anvil 3. The opening in the coronary artery 11 may e.g. have been formed according to the method described in the international application with publication No. WO 95/17127 with the title "Method and instrument for establishing the receiving side of a coronary artery bypass graft".

Figure 4:
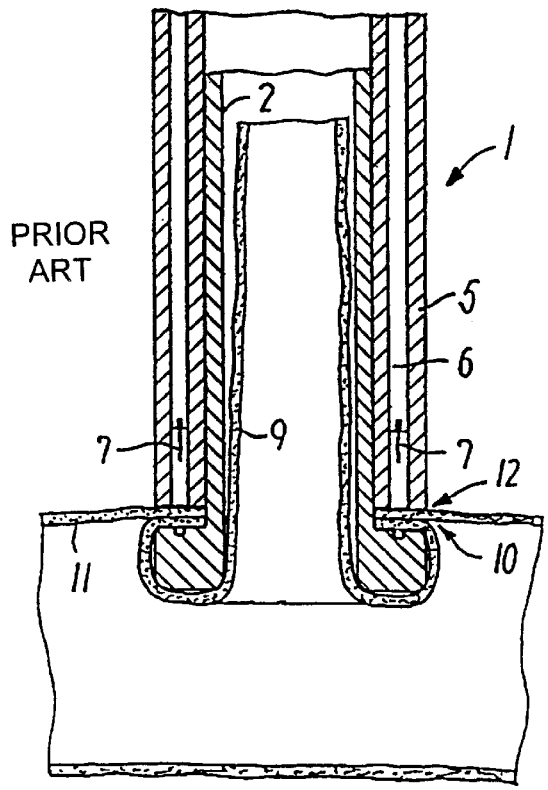
Figure 5:
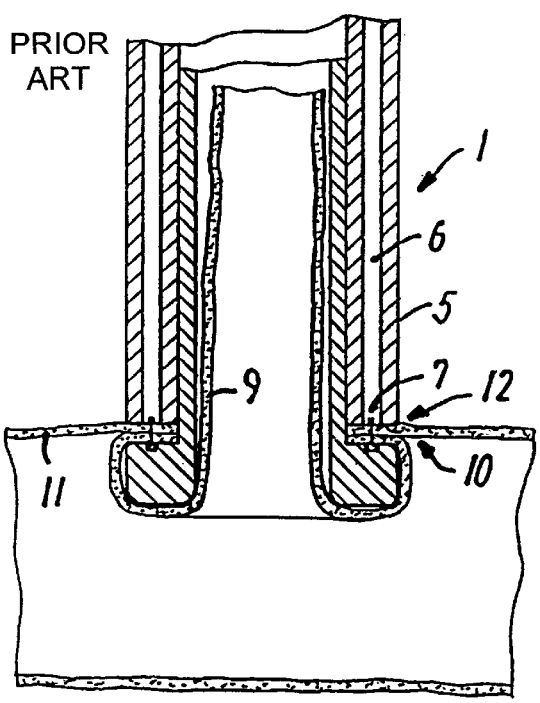

As soon as the operating surgeon in the situation shown in FIG. 3 has ascertained that the edge region 12 embraces the anvil tube 2 closely on all sides, he or she will proceed to the situation shown in FIG. 4, in which the clamping tube 5 has been moved towards the anvil 3 so as to clamp the edge region 12 on the coronary artery 11 and the end region 10 on the bypass vessel 9 firmly together in readiness for the next step shown in FIG. 5, in which the stapling plungers 6 have been moved downwardly so as to cause the staples 7 to penetrate the edge region 12 and the end region 10 and engage the staple-bending recesses 4, by which they will be bent inwards in a tangential direction in a similar manner to what is known from both surgical staplers and ordinary office staplers.

Figure 6:
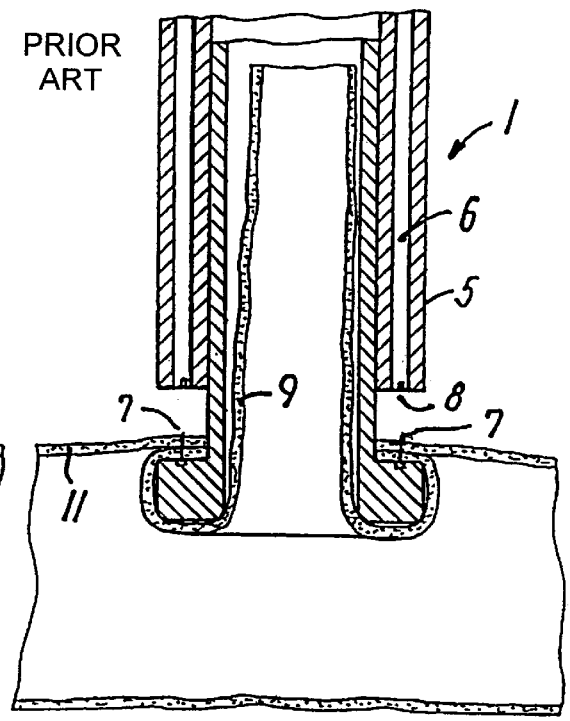

In the situation shown in FIG. 6, the clamping tube 5 together with the stapling plungers 6 have been moved outwardly and away from the staples 7, the staple-holding recesses 8 due to their light holding action having let go of the staples 7, the latter also having been anchored in the end region 10 by their bent ends.

Figure 7:
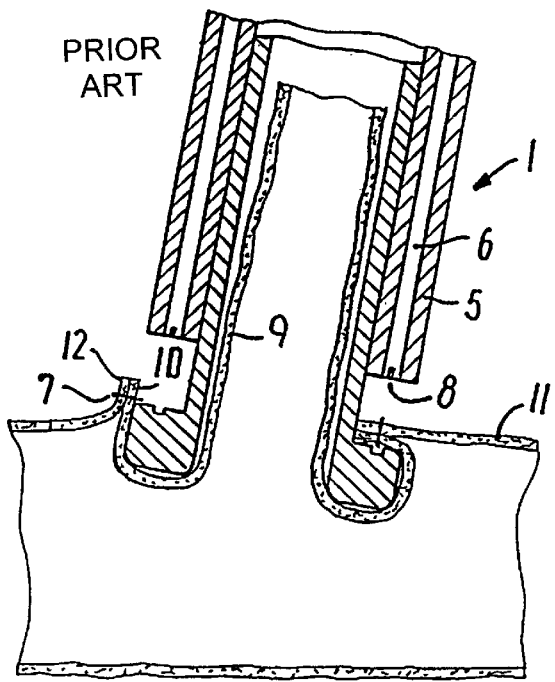
Figure 8:
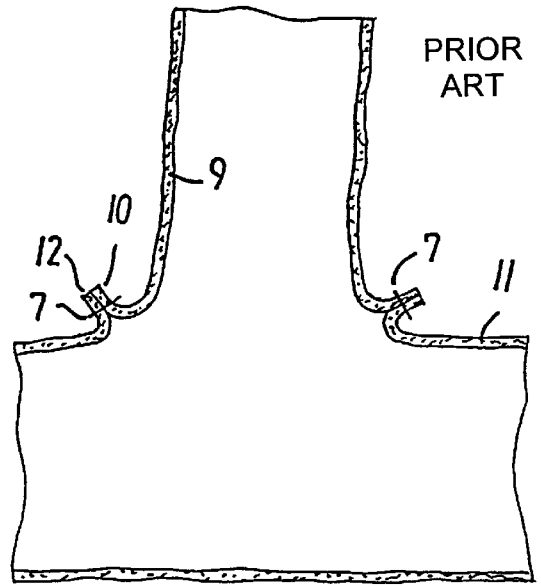

FIG. 7 shows the situation, in which the operation of removing the anastomosis instrument 1 from the coronary artery 11 and its anastomosis with the bypass vessel 9 has begun. As will be seen from FIGS. 6 and 7, the circumferential pocket formed by the eversion of the lower end of the bypass vessel 9 will now open and allow the anvil 3 to be removed by luxation, FIG. 8 showing the situation after such removal, resulting in a finished anastomosis of the intima-to-intima type considered most desirable for this type of operation.

The three main components of the anastomosis instrument 1 referred to above, i.e. the anvil tube 2, the clamping tube 5 and the set of stapling plungers 6, will, of course, have to be connected to some kind of operating members to enable the operating surgeon and his or her assistants to carry out the steps shown in FIGS. 1–8. Theoretically, these operating members could consist of three tubes (not shown), viz.

a relatively long holding tube in continuation of the anvil tube 2, a somewhat shorter clamping tube in continuation of the clamping tube 5, and an even shorter stapling tube, to which the stapling plungers 6 are connected.

As is well-known, however, coronary bypass operations, especially according to the method subject to the international application No. WO 95/17127 entitled "Method and instrument for establishing the receiving site of a coronary artery bypass graft", should be carried out as rapidly as possible, and for this reason, the "theoretical" embodiment shown in FIGS. 1–7 is too cumbersome to work with to ensure a sufficiently rapid operating procedure. As mentioned above, FIGS. 9–22 illustrate an embodiment of an anastomosis instrument according to the present invention, that is highly suitable for creating an end-to-side anastomosis in a very short time.

In FIGS. 9–22, those of the components functionally corresponding to components shown in FIGS. 1–7 have been given the same reference numbers with 500 added, whereas components not having "opposite numbers" in FIGS. 1–7 have been given the reference numbers of the components, with which they are most closely related, with the addition of a capital letter.

Figure 9:
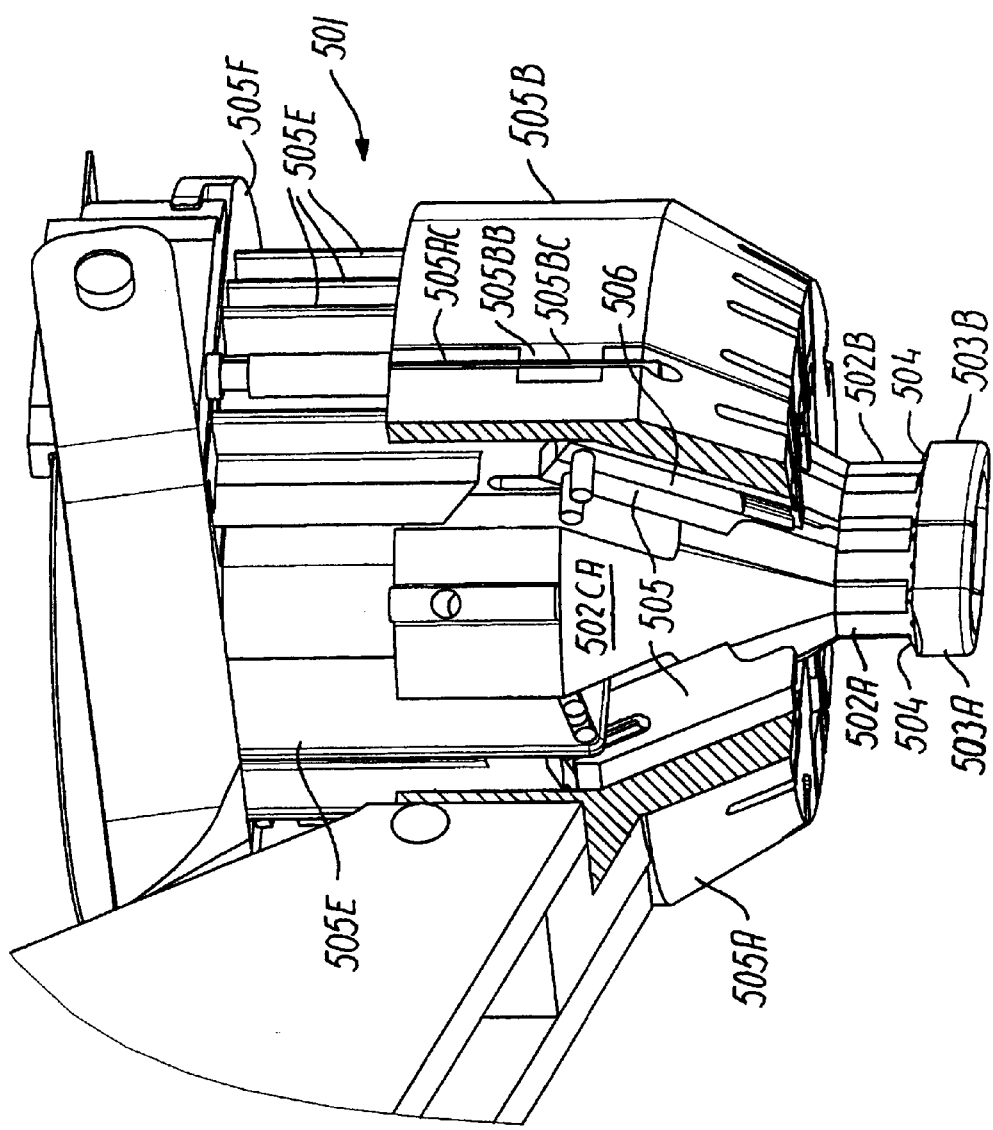

As shown in FIG. 9, the anastomosis instrument 501 comprises a number of parts functionally related to parts of the instrument shown in FIGS. 1–7, viz.:

an anvil tube 502A, 502B, an anvil 503A, 503B, a set of clamping slides 505, slidable in a clamping-slide housing 505A, 505B, and a set of stapling plungers 506 slidable in said clamping slides 505.

Although the basic functions of these parts are the same as the basic functions of related parts in the embodiment of FIGS. 1–7, the arrangement differs somewhat from that of the latter, as will be evident from the following.

Thus, the anvil tube 502A, 502B of FIG. 9 is an extension of a core member 502CA, 502CB, cf. also FIG. 15, a central passage 502D extending all the way through both the core member 502CA, 502CB and the anvil tube 502A, 502B so as to make it possible to place a bypass vessel in the passage in the same manner as shown in FIG. 2, showing a bypass vessel 9 placed in the anvil tube 2.

The rear face of the anvil 503A, 503B, facing upwardly in FIG. 9, is provided with a number of staple-bending recesses 504 substantially evenly distributed about the anvil and each adapted to co-operate with a respective one of the stapling plungers 506.

The clamping slides 505 are adapted to slide in a direction making an angle of substantially 30° with the longitudinal axis of the passage 502D, being guided for such movement by guideways formed in the inside of the slide housing 505A, 505B and in the outside of the core member 502CA, 502CB.

Similarly, each of the stapling plungers 506 is adapted to slide in substantially the same direction in a guideway in a respective one of the clamping slides 505. Both the clamping slides 505 and the stapling plungers 506 are provided with short operating studs 505C and 506C, respectively, for co-operation with angular operating slots 505D formed in operating slides 505E adapted to slide in guideways formed in the inside of the slide housing 505A, 505B and in the outside of the core member 502CA, 502CB in a direction substantially parallel to the longitudinal axis of the passage 502D.

All the operating slides 505E are connected to a common operating head 505F, the latter in turn being connected to one arm 505G of a pair of tongs 505G, 505H adapted to be operated manually by the surgeon, the other arm 505H being connected to the core member 502A, 502B and the clamping-slide housing 505A, 505B.

Figure 12:
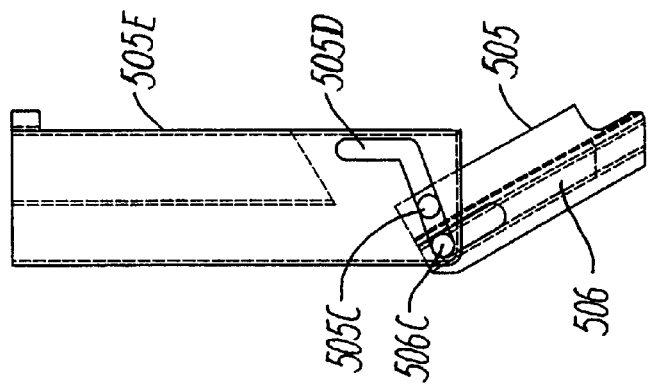
FIGS. 12–14 are side views of a staple-pusher set consisting of a stapling plunger, a clamping slide and their common operating slide in positions corresponding to those shown in FIG. 9–11, respectively.

When an anastomosis is to be established according to the principles explained above with reference to FIGS. 1–8, the first step is, with the mutually movable parts in the positions shown in FIGS. 9 and 12 and with the stapling plungers 506 "loaded" with staples (not shown), to place a bypass vessel in the passage 502D and evert its forward (lower) end about the anvil 503A, 503B in the manner shown in FIG. 2. The next step is to insert the anvil 503A, 503B with the everted end of the bypass vessel into an opening formed in the side of, say, a coronary artery in the manner shown in FIG. 3. These two steps are suitably carried out using the pair of tongs 505G, 505H as a "handle".

Figure 13:
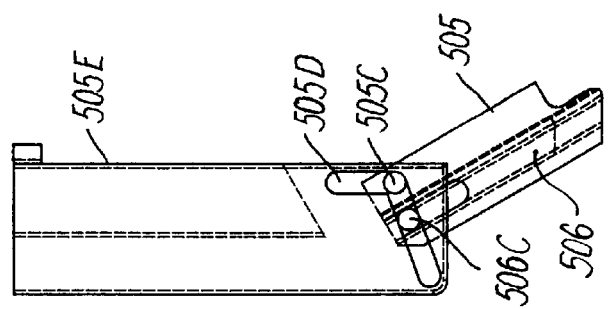
Figure 10:
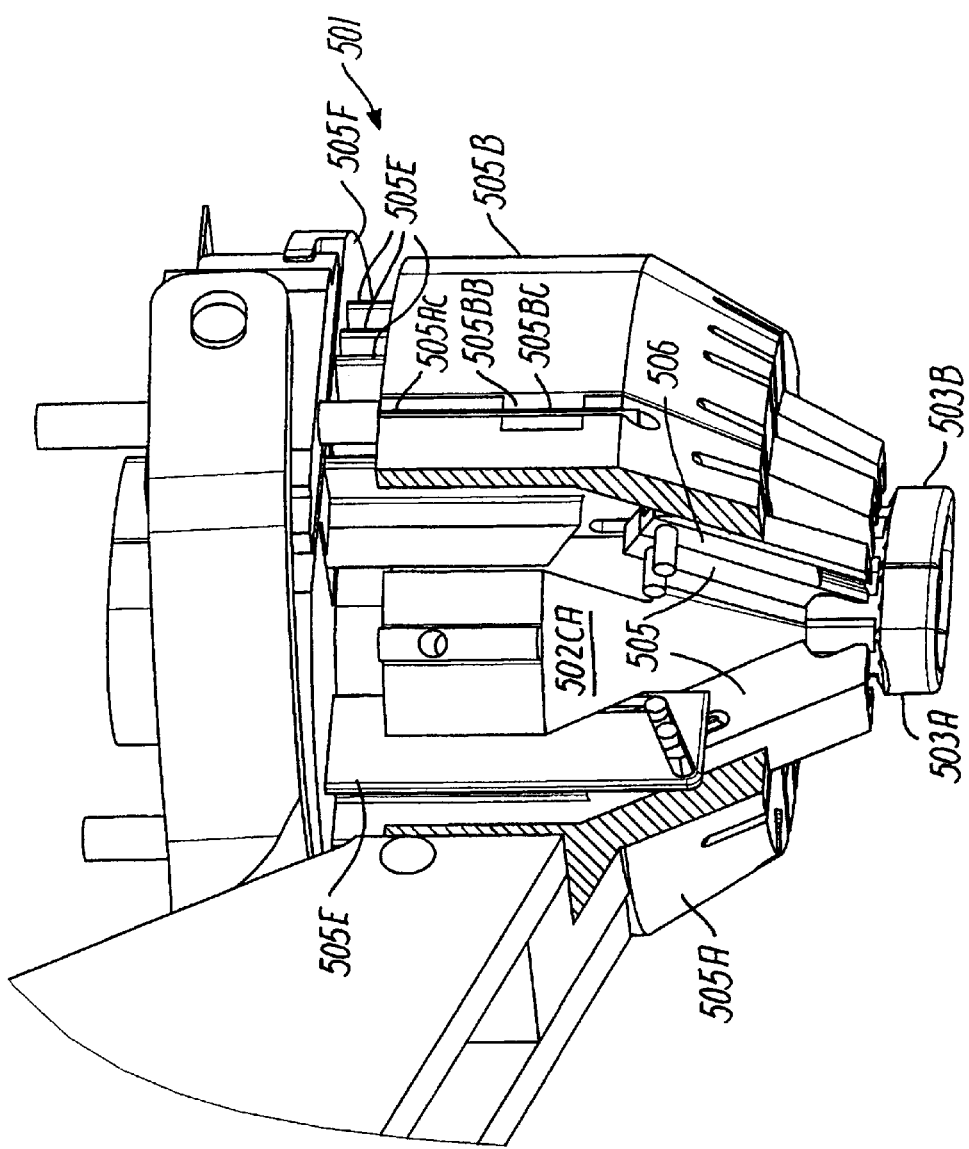

When the surgeon has ascertained that the bypass vessel is in the correct position relative to the artery, she or he will press the arm 505G towards the arm 505H, thus causing the common operating head 505F to move the operating slides 505E forward (downward), vide FIGS. 10 and 13, so as to bring the clamping slides 505, moved by the co-operation between the oblique parts of the operating slots 505D and the operating studs 505C, close to the rear (upper) face of the anvil 503A, 503B, thus creating a situation analogous to that shown in FIG. 4. At this point it should, however, be noted that the oblique forward (downward) and inward movement of the clamping slides cause their forward end to exert a certain inwardly directed force on the tissues thus being clamped, thus counteracting any tendency for these tissues to slip off from the anvil.

Figure 14:
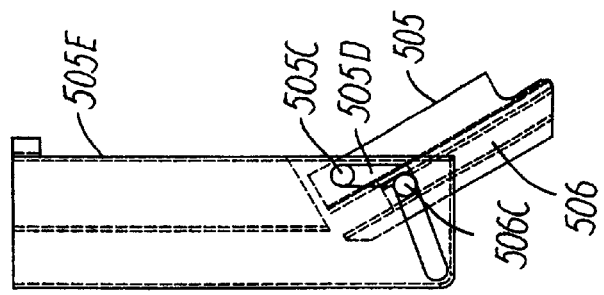
Figure 11:
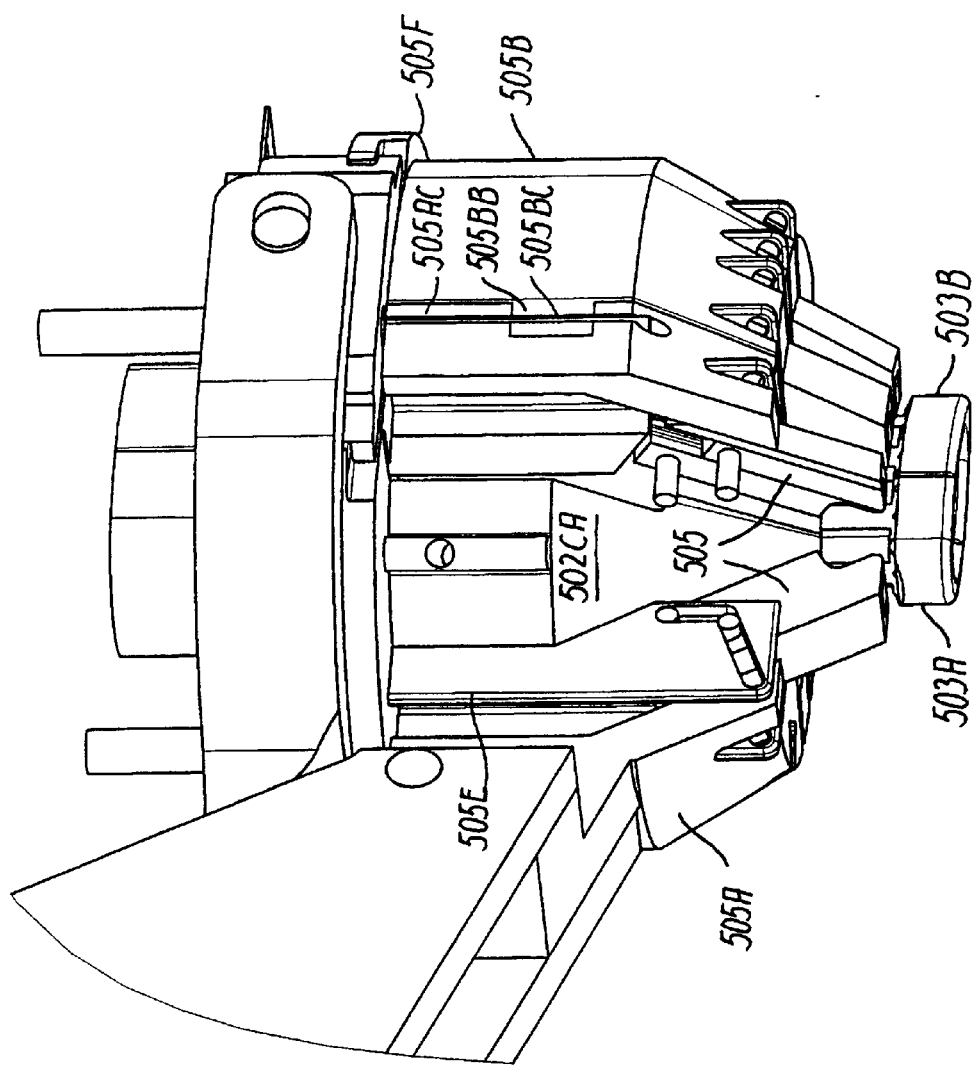

Continued movement of the arm 505G towards the "stationary" arm 505H will, of course, create further forward (downward) movement of the operating slides 505E, vide FIGS. 11 and 14. The in-line parts of the operating slots 505D will now hold the clamping slides 505 in a clamping position, holding the tissues to be joined in the same manner as shown in FIG. 4, while the final part of the movement will cause the oblique parts of the operating slots 505D to advance the stapling plungers 506 and cause the latter to insert the staples (not shown) and bend them in co-operation (in contact) with the staple-bending recesses 504 in the same manner as shown in FIG. 5. All of these recesses are (of course) placed at an outwardly directed angle of same substantially 30°.

At this point, the anastomosis has been established, after which the instrument can be removed according to the principles illustrated by FIGS. 6–8, the surgeon previously having released the pressure on the arm 505G, allowing the spring 505I to act in the opposite direction, causing the parts 506, 505, 505E and 505F to return to the positions shown in FIG. 9. If the core member 502CA, 502CB and the clamping slide housing 505A, 505B were unitary components, i.e. each made in one piece, this removal would have to be effected by pulling the instrument away from the anastomosis towards the free end of the bypass vessel (not shown). One prerequisite for so doing is, obviously, that such a free end exists, i.e. that the bypass vessel is not part of an anastomosis at the other end.

In order to make it possible to remove the instrument from a bypass vessel without a free end, the components surrounding it, i.e. surrounding the passage 502D, are constituted by downstream parts 502CA, 505A and 503A and upstream parts 502CB, 505B and 503B, respectively of the core member, the clamping-slide housing and the anvil, respectively. (The expressions "upstream" and "downstream" refer to the direction of flow in the coronary artery being operated upon when the instrument is placed in the preferred orientation relative to the artery, i.e. with the blood flowing towards the left in FIG. 15).

The upstream part 505B of the housing 505A, 505B is releasably connected to the downstream part 505A by means of hook-and-pin connections, cf. FIGS. 9, 16 and 21, constituted by recesses 505AB in the downstream part 505A adapted to receive projections 505BB on the upstream part, holding slots 505AC and 505BC being formed in alignment with the recesses 505AB and the projections 505BB, respectively, and adapted to receive removable holding pins 505K.

When the core member 502CA, 502CB and the clamping-slide housing 505A, 505B are assembled with the holding pins 505K in place as shown in FIGS. 9 and 16, the housing 505A, 505B will keep the core member 502CA, 502CB from coming apart. Conversely, when the holding pins 505K have been pulled up, both the housing 505A, 505B and the core member 502CA, 502CB can easily be divided by simply pulling them apart, thus making it possible to remove the apparatus from the bypass vessel in a lateral direction. During this operation of dividing the core member and the housing, the various parts associated with them will, of course, have to be divided or liberated. The means for achieving this are not shown in detail, as any normally skilled mechanical technician or toolmaker should be able to devise the requisite mechanism without further guidance from the present description.

What is claimed is:

1. A method of connecting an end region of a first vessel to a side of a second vessel by carrying out an end-to-side anastomosis, said method comprising the steps a–d:

a) forming an opening in the side of said second vessel, b) inserting in said opening an anastomosis instrument carrying said first vessel in a longitudinal cavity thereof and with said end region everted about a circumferential anvil member constituting a forward portion of said instrument in such a manner that the intima side of said end region comes into contact with the intima side of said second vessel at an edge region of said opening, c) joining said end region to said edge region by inserting penetratingly therethrough and leaving therein a plurality of spiked members, and d) removing said instrument from the joint formed between said first and second vessels, said steps a–d being carried out by e) the use of said anastomosis instrument comprising
  e1) an anvil assembly comprising said circumferential anvil member and in which said first vessel may be placed with its end region everted about said anvil member with the terminal part of said end region facing rearwardly,
  e2) rearwardly facing staple-bending recesses provided in said anvil member,
  e3) clamping members adapted to be moved towards said anvil member so as to make it possible to clamp together therebetween said end region on said first vessel and an edge region on said second vessel, and
  e4) stapling plungers movable relative to said anvil member and adapted to insert staples penetratingly through said clamped end and edge regions into engagement with said stapling-bending recesses so as to bend permanently said staples into a shape by which said staples hold said end and edge regions together, characterized by f) said joining step including the step of sliding said stapling plungers in directions forming acute angles with the longitudinal axis of said longitudinal cavity so that said staples converge in a region forward of said circumferential anvil member.

2. A method of connecting as claimed in claim 1, wherein said joining step further includes the step of sliding said clamping members at acute angles parallel to those in which adjacent ones of said stapling plungers are slidable.

3. A method of connecting as claimed in claim 1, surrounding said passage are releasably interconnected so as to enable said passage to be split lengthwise, wherein said anvil assembly and said clamping members surrounding said longitudinal cavity are respectively formed of two releasably interconnected parts, and where said removing step includes the step of splitting said passage lengthwise by releasing an interconnection between said interconnected parts.

4. An anastomotic instrument for connecting an end region of a first vessel to a side of a second vessel by carrying out an end-to-side anastomosis, comprising:

a longitudinal cavity in which said first vessel is carried, an anvil assembly located about said longitudinal cavity and comprising a circumferential anvil member about which an end region of said first vessel may be everted with the terminal part of said end region facing rearwardly, rearwardly facing staple-bending recesses provided in said anvil member and about said longitudinal cavity, clamping members about said longitudinal cavity adapted to be moved towards said anvil member so as to make it possible to clamp together therebetween said end region on said first vessel and an edge region on said second vessel, and stapling plungers about said longitudinal cavity movable relative to said anvil member and adapted to insert staples penetratingly through said clamped end and edge regions into engagement with said stapling-bending recesses so as to bend permanently said staples into a shape by which said staples hold said end and edge regions together, said stapling plungers being slidable in directions forming acute angles with the longitudinal axis of said longitudinal cavity and converging in a region forward of said circumferential anvil member.

5. An instrument as claimed in claim 4, wherein said clamping members are slidable at acute angles parallel to those in which adjacent ones of said stapling plungers are slidable.

6. An instrument as claimed in claim 4, wherein said anvil assembly is formed of first interconnectable parts surrounding said longitudinal cavity, said anvil member is formed of second interconnectable parts surrounding said longitudinal cavity, and said clamping members are formed respectively of third and fourth interconnectable parts surrounding said longitudinal cavity, and further including a releasable interconnection between said interconnected parts so as to enable said longitudinal cavity to be split lengthwise.

7. An instrument claim 5, wherein a) said clamping members are provided with first laterally extending operating studs, b) said stapling plungers are provided with second laterally extending operating studs, and c) said first and second operating studs are adapted to cooperate with common angular operating slots in likewise common operating slides adapted to be operated by a manually operable mechanism common to all operating slides such that c1) in an initial phase of movement of said operating slides, the clamping members move into close adjacency to said anvil member, and c2) in a final phase of movement of said operating slides, the stapling plungers move into a staple-bending position close to said anvil member.

* * * * *